(12) United States Patent
Kim et al.

(10) Patent No.: US 11,701,189 B2
(45) Date of Patent: Jul. 18, 2023

(54) DEVICE FOR PROVIDING JOINT REPLACEMENT ROBOTIC SURGERY INFORMATION AND METHOD FOR PROVIDING SAME

(71) Applicant: CUREXO, INC., Seoul (KR)

(72) Inventors: Bong Oh Kim, Seoul (KR); Dae Guk Do, Seoul (KR); Soo Jong Kim, Seoul (KR)

(73) Assignee: CUREXO, INC., Seoul (KR)

( * ) Notice: Subject to any disclaimer, the term of this patent is extended or adjusted under 35 U.S.C. 154(b) by 0 days.

(21) Appl. No.: 17/796,347

(22) PCT Filed: Jan. 26, 2021

(86) PCT No.: PCT/KR2021/001038
§ 371 (c)(1),
(2) Date: Jul. 29, 2022

(87) PCT Pub. No.: WO2021/153973
PCT Pub. Date: Aug. 5, 2021

(65) Prior Publication Data
US 2023/0079638 A1    Mar. 16, 2023

(30) Foreign Application Priority Data

Jan. 31, 2020  (KR) .................. 10-2020-0011496

(51) Int. Cl.
*A61B 34/30*  (2016.01)
*A61B 34/10*  (2016.01)
*A61B 34/00*  (2016.01)

(52) U.S. Cl.
CPC ............. *A61B 34/30* (2016.02); *A61B 34/10* (2016.02); *A61B 34/25* (2016.02);
(Continued)

(58) Field of Classification Search
CPC ......... A61B 34/30; A61B 34/10; A61B 34/25; A61B 2034/107; A61B 2034/108; A61B 2034/252; A61B 2034/258
See application file for complete search history.

(56) References Cited

U.S. PATENT DOCUMENTS

2015/0305828 A1   10/2015  Park et al.
2017/0312031 A1*  11/2017  Amanatullah ......... A61B 34/10
2021/0093400 A1*  4/2021   Quaid .................... A61B 34/76

FOREIGN PATENT DOCUMENTS

EP     3581121 A1    12/2019
KR   10-1480251 B1    1/2015
(Continued)

OTHER PUBLICATIONS

Mako PKA Application User Guide, 2018.

*Primary Examiner* — Basil T. Jos
(74) *Attorney, Agent, or Firm* — Bridgeway IP Law Group, PLLC; Jihun Kim (57) ABSTRACT

A device for providing joint replacement robotic surgery information comprises: a memory unit configured to store surgery plan information set before surgery including a cutting path of a surgical target bone; a target acquisition unit configured to acquire positions of a plurality of cutting target points forming the cutting path based on the surgery plan information; a robot position calculation unit configured to calculate a current cutting position of the surgical robot among the cutting target points based on surgery progress of the surgical robot; a graphic user interface (GUI) providing unit configured to generate graphics that represent surgery progress information including a current cutting position of the surgical robot and positions of the cutting target points on a virtual bone model corresponding to the surgical target bone; and a display unit configured to display the virtual bone model and the surgery progress information.

8 Claims, 9 Drawing Sheets

(52) U.S. Cl.
CPC ... *A61B 2034/107* (2016.02); *A61B 2034/108* (2016.02); *A61B 2034/252* (2016.02); *A61B 2034/258* (2016.02)

(56) References Cited

FOREIGN PATENT DOCUMENTS

| | | |
|---|---|---|
| KR | 10-2015-0039801 A | 4/2015 |
| KR | 10-2015-0125069 A | 11/2015 |
| KR | 10-2019-0000940 A | 1/2019 |
| KR | 10-2019-0030414 A | 3/2019 |
| WO | 2006-091494 A1 | 8/2006 |
| WO | 2014-022786 A2 | 2/2014 |
| WO | 2014-028563 A1 | 2/2014 |
| WO | 2017-151863 A1 | 9/2017 |
| WO | 2017-204832 A1 | 11/2017 |

* cited by examiner

DEVICE FOR PROVIDING JOINT REPLACEMENT ROBOTIC SURGERY INFORMATION AND METHOD FOR PROVIDING SAME

TECHNICAL FIELD

The disclosure relates to a device and method for providing robotic surgery information, and more particularly to a device and method for providing information about the progress of surgery while artificial joint replacement surgery is performed by a robot.

BACKGROUND ART

Since robotic surgery was first performed using the ROBODOC in 1994, surgical robots have recently been variously utilized in the fields of orthopedic surgery including artificial joint replacement surgery such as knee joint replacement surgery and hip joint replacement surgery, and robot systems for the surgical robots have also been continuously developed.

As compared with a surgeon's manual surgery, the robotic surgery not only increases the accuracy of surgery and the satisfaction of a patient but has also been reported to reduce complications that may occur after the surgery. Therefore, the proportion of robotic surgery in the fields of orthopedic surgery is expected to gradually increase.

The robotic surgery is broadly classified into passive robotic surgery, semi-active robotic surgery, and active robotic surgery. In the passive robotic surgery, a surgeon controls a robot in person to perform surgery throughout the process of surgery. In the semi-active robotic surgery, a surgeon uses a robot to perform cutting or the like process, but the robot serves to limit a surgical tool moved by the surgeon to a preset path through haptic feedback or the like in the foregoing process. On the other hand, in the active robotic surgery, a robot automatically conducts surgery based on preoperative planning without a surgeon's intervention.

Unlike the passive or semi-active robotic surgery, the active robotic surgery has problems in that surgery information is not present because a surgeon's intervention is excluded. Here, the surgery information allows the surgeon to monitor the progress of surgery, such as whether a robot is currently conducting surgery accurately along a preoperative planning path, the speed at which the robot is currently operating, the load that the robot is receiving, etc. Therefore, a surgeon may injure when s/he is positioned on a path where a robot moves to cut a bone, and it may be difficult for a surgeon to quickly grasp the wrong movement of a robot even though the robot is moving along a wrong path, thereby posing a great risk to a patient.

However, a conventional surgical robot system does not provide any surgery information or, even if provided, merely provides extremely limited information such as a bone image or the like after the cutting is completed, thereby providing no information to grasp a robot's current progress or situations to be carried out in the future, etc. as a whole.

Accordingly, there is a need for providing surgery information that allows a surgeon to quickly grasp a surgical path on which a robot moves or the state of the robot in the progress of surgery. In particular, it is more necessary to provide such surgery information in the active robotic surgery from which a surgeon's intervention is excluded.

DISCLOSURE

Technical Problem

The disclosure is proposed to solve the aforementioned problems, and an aspect of the disclosure is to provide a device and method for providing surgery information that allows a surgeon to grasp a surgical path for a robot or the state of the robot in the progress of joint replacement robotic surgery.

Technical Solution

According to an embodiment of the disclosure, a device for providing information about joint replacement robotic surgery includes: a memory unit configured to store surgery plan information set before surgery including a cutting path of a surgical target bone; a target acquisition unit configured to acquire positions of a plurality of cutting target points forming the cutting path based on the surgery plan information; a robot position calculation unit configured to calculate a current cutting position of the surgical robot among the cutting target points based on surgery progress of the surgical robot; a graphic user interface (GUI) providing unit configured to generate graphics that represent surgery progress information including a current cutting position of the surgical robot and positions of the cutting target points on a virtual bone model corresponding to the surgical target bone; and a display unit configured to display the virtual bone model and the surgery progress information.

Here, the device may further include a view switching unit configured to switch a view of the virtual bone model displayed on the display unit according to parts of the surgical target bone that undergoes cutting of the surgical robot.

Meanwhile, the target acquisition unit may perform coordinate transformation from a position of the cutting target point in a first coordinate system based on an implant to be replaced in the surgical target bone to a position in a second coordinate system based on the virtual bone model.

In addition, the robot position calculation unit may estimate a current cutting position of the surgical robot based on a cutting speed of the surgical robot based on the surgery plan information and a distance between the cutting target points.

Here, the device may further include a notification unit configured to provide a notification when an actual cutting position of the surgical robot based on information received from a tracking device configured to track the position of the surgical robot is far by more than a predetermined distance away from the estimated current cutting position of the surgical robot.

Further, the robot position calculation unit may calculate a current cutting position of the surgical robot based on information received from a tracking device configured to track the position of the surgical robot.

Meanwhile, the device may further include a signal receiver configured to receive state information of the surgical robot from the surgical robot, wherein the display unit displays the state information of the surgical robot.

In addition, the GUI providing unit may set whether to display the surgery progress information through the display unit based on on/off states of the surgical robot.

Further, the GUI providing unit may generate figures respectively corresponding to the plurality of cutting target points, a cutting line formed by connecting the cutting target points, and a figure corresponding to the current cutting position of the surgical robot.

Further, the GUI providing unit may generate graphics based on a cutting line formed by connecting the cutting target points, so that the cutting line that the surgical robot has already passed and the cutting line that the surgical robot is currently passing can be distinguished from each other with respect to the current cutting position of the surgical robot calculated by the robot position calculation unit.

Besides, according to another embodiment of the disclosure, a method of providing information about joint replacement robotic surgery, steps of which are performed by a joint replacement robotic surgery information providing device that provides information about joint replacement robotic surgery includes the steps of: storing surgery plan information set before surgery including a cutting path of a surgical target bone; acquiring positions of a plurality of cutting target points forming the cutting path based on the surgery plan information; calculating a current cutting position of the surgical robot among the cutting target points based on surgery progress of the surgical robot; generating graphics that represent surgery progress information including a current cutting position of the surgical robot and positions of the cutting target points on a virtual bone model corresponding to the surgical target bone; and displaying the virtual bone model and the surgery progress information on a display unit.

Here, the method may further include switching a view of the virtual bone model displayed on the display unit according to parts of the surgical target bone that undergoes cutting of the surgical robot.

Meanwhile, the step of calculating the current cutting position of the surgical robot may include estimating a current cutting position of the surgical robot based on a cutting speed of the surgical robot based on the surgery plan information and a distance between the cutting target points.

Further, the step of generating graphics based on the surgery progress information may include generating figures respectively corresponding to the plurality of cutting target points, a cutting line formed by connecting the cutting target points, and a figure corresponding to the current cutting position of the surgical robot.

In addition, the step of generating graphics based on the surgery progress information may include generating graphics based on a cutting line formed by connecting the cutting target points, so that the cutting line that the surgical robot has already passed and the cutting line that the surgical robot is currently passing can be distinguished from each other with respect to the current cutting position of the surgical robot.

Advantageous Effects

As described above, according to the disclosure, a cutting path planned before surgery, surgery progress information about which position a surgical robot is currently passing on the cutting path, and the state information of the surgical robot are provided to a user, thereby helping the user to recognize the surgical progress and monitor the surgical progress.

MODE FOR INVENTION

Below, specific embodiments of the disclosure will be described with reference to the accompanying drawings. However, detailed descriptions about well-known functions or configurations, which may obscure the gist of the disclosure, in the following description and accompanying drawings will be omitted. Further, like numerals refer to like elements throughout the accompanying drawings.

For reference, the joint replacement robotic surgery disclosed in the present specification includes knee-joint replacement robotic surgery and hip-joint replacement robotic surgery. Below, the knee joint replacement robotic surgery will be described as an example of the joint replacement robotic surgery.

Figure 1:
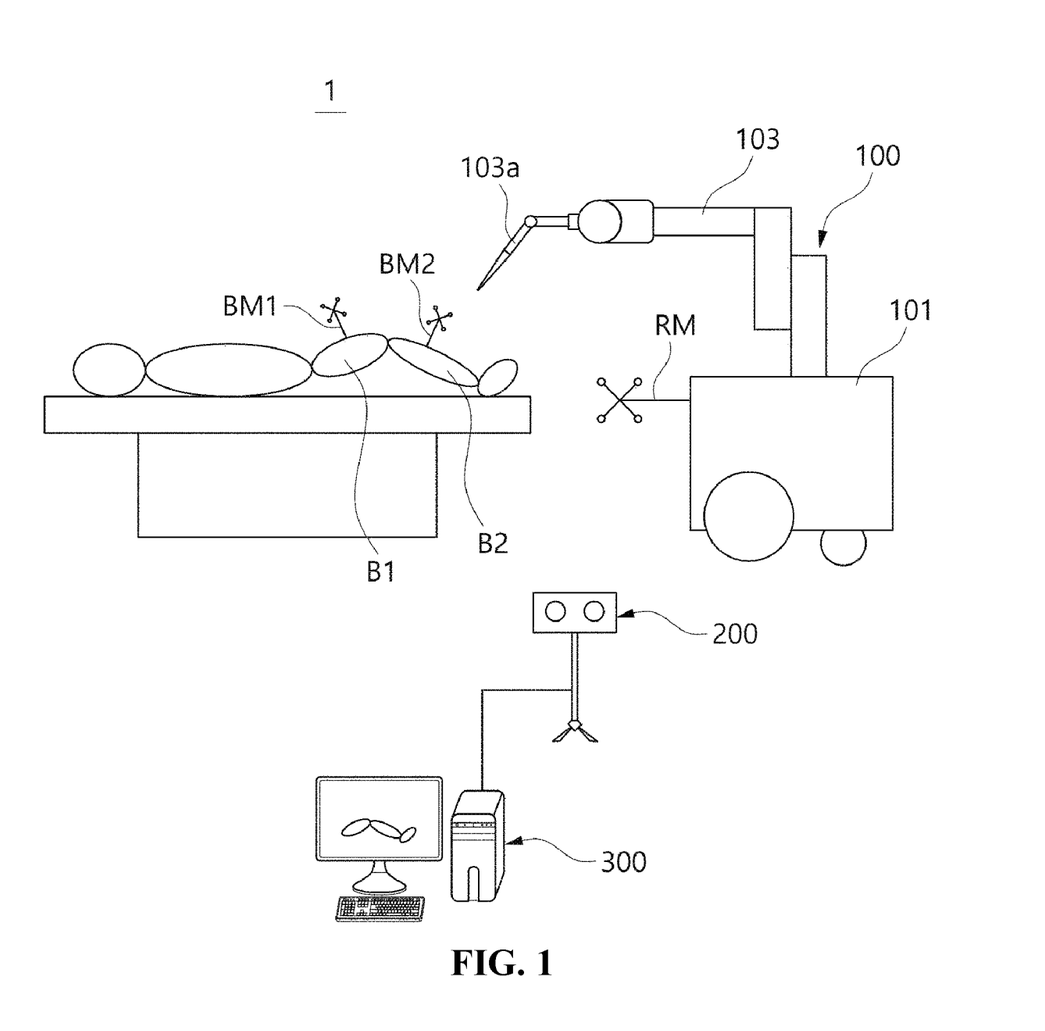
FIG. 1 is a diagram showing a schematic configuration of a joint replacement robotic surgery system including a device for providing information about joint replacement robotic surgery according to an embodiment of the disclosure.

FIG. 1 is a diagram showing a schematic configuration of a joint replacement robotic surgery system 1 including a device for providing information about joint replacement robotic surgery according to an embodiment of the disclosure;

Referring to FIG. 1, a joint replacement robotic surgery system 1 placed in a surgical site includes bone markers BM1 and BM2 fixed to surgical target bones B1 and B2, a surgical robot 100, a tracking device 200, and a device 300 for providing information about the joint replacement robotic surgery.

The surgical target bones B1 and B2 refer to bones to be subjected to the robotic surgery, and, for example, FIG. 1 shows a femur B1 and a tibia B2. The bone markers BM1 and BM2 are respectively fixed to the femur B1 and the tibia B2, and used as the references for tracking the positions of the femur B1 and the tibia B2 during surgery.

The surgical robot 100 refers to a robot that performs surgery for joint replacement, and includes a robot base 101 and a robot arm 103. Various surgical tools 103a such as a burr drill, for bone cutting, etc., may be coupled to an end effector, i.e., the end of the robot arm 103. Further, the surgical robot 100 may be mounted with various sensors to sense the states of the surgical robot 100, such as the load applied to the coupled surgical tool, the speed at which the robot is operating, etc. A robot marker RM is fixed to the base 101 of the surgical robot 100 and used as the reference for tracking the surgical robot 100 during surgery.

For reference, passive or active optical markers may be used as the bone markers BM1 and BM2 and the robot marker RM. The optical marker includes a plurality of bar members shaped like branches and branched in different directions with respect to a central point. Each bar may be formed with a ball marker at the end portion thereof. This shape of the optical marker is merely an example. Of course, the optical marker may have various other publicly-known shapes.

The tracking device 200 may be implemented as an optical tracking System (OTS) to track the positions and poses of the bone markers BM1 and BM2 fixed to the surgical target bones B1 and B2 and the robot marker RM fixed to the surgical robot 100. For reference, the optical tracking system refers to a system that is capable of tracking the position and pose in a 3-dimensional space in real time by using two infrared cameras to track the marker and converting a distance based on triangulation. The tracking principle of such an optical tracking system is well known, and therefore detailed descriptions thereof will be omitted for the convenience of description.

The device 300 for providing information about the joint replacement robotic surgery (hereinafter referred to as a 'surgery information providing device') generates and provides surgery progress information when the surgical robot 100 performs surgery on the surgical target bones B1 and B2. Here, the surgery progress information includes information about a cutting path where the surgical target bones B1 and B2 are cut by the surgical robot 100, a cutting position at which the surgical robot 100 is currently performing the cutting, and the state of the surgical robot 100.

The surgery information providing device 300 may be implemented to include a computer (or a processor) and a display unit. FIG. 1 shows that the surgery information providing device 300 is implemented as a separate device physically divided from the surgical robot 100. However, as necessary, the processor of the surgery information providing device 300 may be placed in the surgical robot 100, and the display may be connected to and installed together with the tracking device 200, so that the processor and the display unit can exchange various pieces of information through a communication module.

Figure 2:
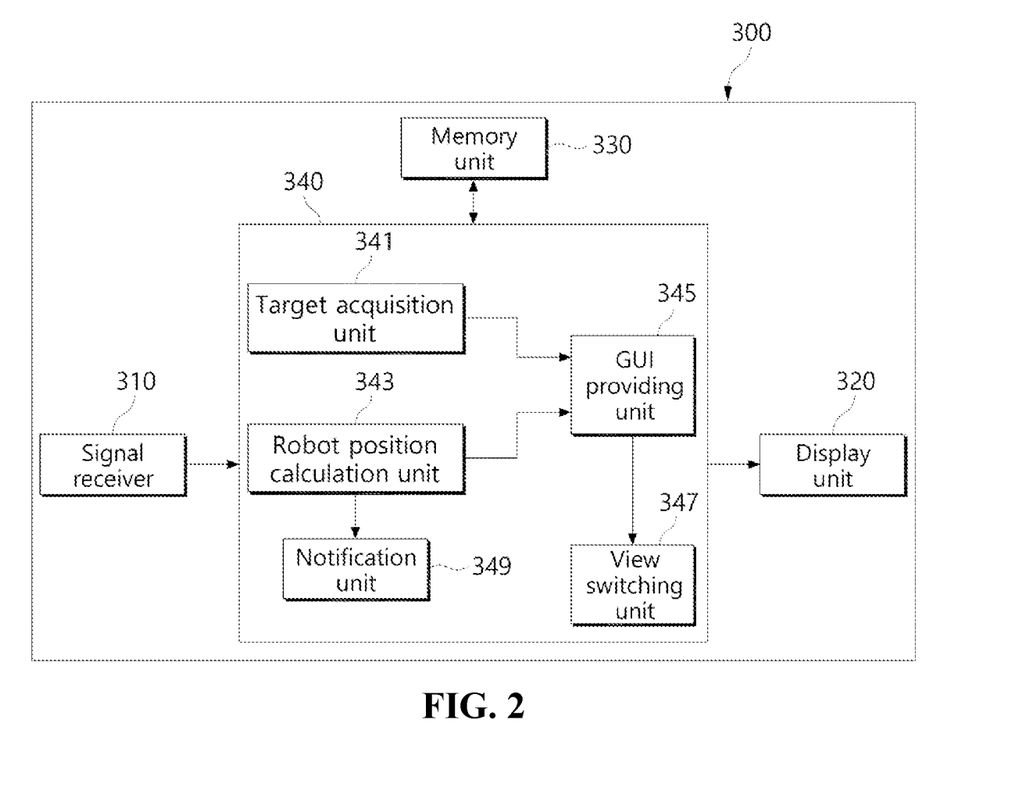
FIG. 2 is a block diagram showing a detailed configuration of a device for providing information about joint replacement robotic surgery according to an embodiment of the disclosure.

FIG. 2 is a block diagram showing a detailed configuration of the surgery information providing device 300 according to an embodiment of the disclosure. Referring to FIG. 2, the surgery information providing device 300 according to an embodiment of the disclosure includes a signal receiver 310, a display unit 320, a memory unit 330, and a controller 340.

The signal receiver 310 is configured to receive a signal or various pieces of data from the outside, and may, for example, include a high-definition multimedia interface (HDMI) connector and a D-sub connector for connection with an external device, or a communication module for connection with a wired/wireless network such as the Internet. The signal receiver 310 receives various pieces of information from the surgical robot 100 and the tracking device 200. For example, the signal receiver 310 may receive information about various detected robot states from the surgical robot 100, and receive information about the tracked positions and poses of the surgical robot 100 and the surgical target bones B1 and B2 from the tracking device 200.

The display unit 320 is configured to display various pieces of information such as images, graphics, etc. on a screen thereof, and may be implemented as a liquid crystal display (LCD) panel, a light emitting diode (LED) panel, an organic light emitting diode (OLED) panel, etc. The display unit 320 displays surgery progress information, a virtual bone model, etc. while the robotic surgery is in progress. The virtual bone model refers to a 2/3-dimensional bone model reconstructed based on a medical image, e.g., a computerized tomography (CT) image, a magnetic resonance imaging (MM) image, an X-ray image, etc. acquired before surgery and related to a surgical target bone.

The memory unit 330 is implemented as a memory device such as a random-access memory (RAM) or the like, and configured to store various operating systems (OS), middleware, platforms, and various applications for the surgery information providing device 300, and store a program code, processed video and audio signals, and various pieces of data. The memory unit 330 is configured to store a patient's medical image acquired before surgery, the virtual bone model reconstructed based on the medical image, surgical planning information set before surgery, etc. A surgery plan may be made based on the patient's medical image, and the surgical planning information includes information about the types, shapes, sizes, positions, directions of implants to be implanted into the surgical target bones; the cutting path, cutting speed, etc. for the surgical target bone; etc. The cutting path may be variously defined as a straight line, a curved line, or a combination of the straight line and the curved line. In this case, the cutting path or the cutting speed may be integrally or individually planned with respect to each cutting plane.

Figure 3A:
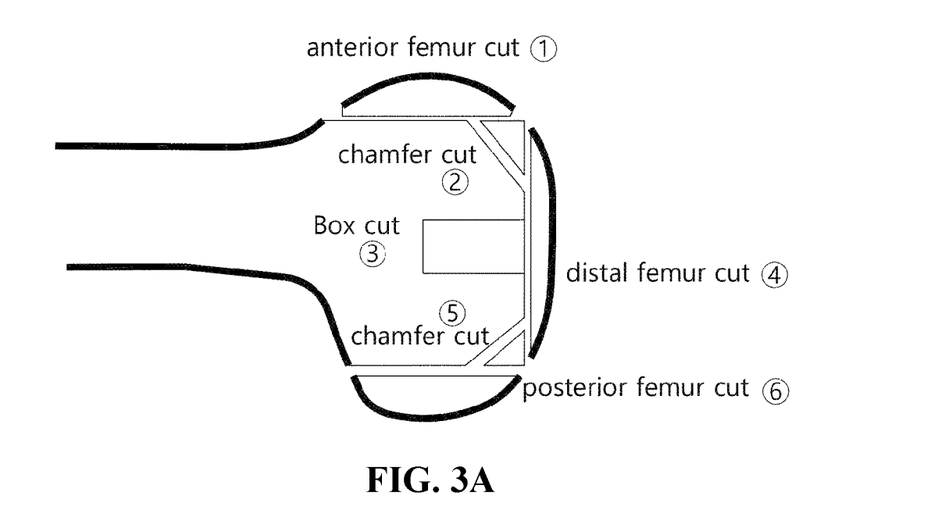
FIGS. 3A-3B are reference diagrams for explaining a cutting path based on surgical planning according to an embodiment of the disclosure.
Figure 3B:
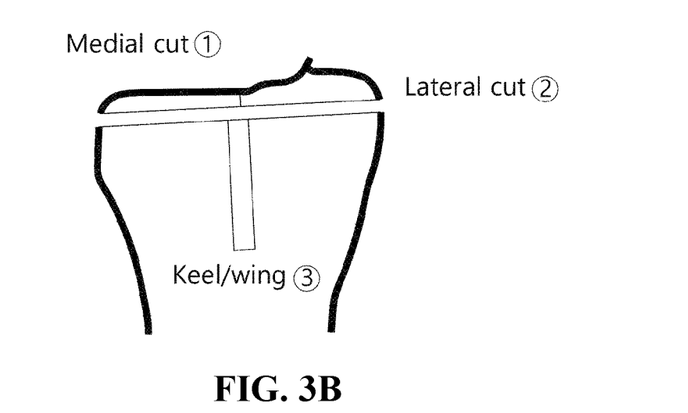

FIGS. 3A-3B are reference diagrams for explaining a cutting path based on surgical planning according to an embodiment of the disclosure, showing the cutting planes of the femur B1 and the tibia B2 during the total knee joint replacement robotic surgery.

Referring to FIGS. 3A-3B, during surgery, the femur is cut on six sides and the tibia is cut on three sides. In this way, when the cutting is performed with respect to the plurality of cutting planes, the surgical planning, which includes the cutting paths corresponding to the cutting planes and the cutting speed on each cutting path, may be individually set for each cutting plane or may be integrally set for all cutting planes.

The controller 340 controls overall operations of the surgery information providing device 300 based on a user command received through a user input unit (not shown) or an internal program. The controller 340 may be implemented including a processor that executes a program and a program code to process and control a signal. The controller 340 may generate and provide graphics based on the surgery progress information corresponding to a robotic surgery process, thereby allowing a user to recognize and monitor the surgery process of the surgical robot 100.

Referring to FIG. 2, the controller 340 includes a target acquisition unit 341, a robot position calculation unit 343, a graphic user interface (GUI) providing unit 345, a view switching unit 347, and a notification unit 349. For reference, the controller 340 is functionally divided into detailed elements, but the controller 340 may be implemented as a software program including instructions for carrying out the functions of the target acquisition unit 341, the robot position calculation unit 343, the GUI providing unit 345, the view switching unit 347, and the notification unit 349, and a processor executing the same.

The target acquisition unit 341 is configured to acquire the positions of a plurality of cutting target points forming the cutting path based on the surgery plan information stored in the memory unit 330. The cutting path may be formed by a set of positional coordinates of the plurality of cutting target points corresponding to a plurality of points.

For reference, during the surgical planning, plans for the shape and size of an implant, and the position and direction of the implant are preceded and the cutting path is set based on the plans for the implant, thereby forming the cutting path in an implant coordinate system based on the origin of the implant. Therefore, as will be described later, to mark the virtual bone model with the cutting path set during the surgical planning, processing is required to transform the positional coordinates of the cutting target points based on the surgical planning into positional coordinates of a bone model coordinate system based on the origin of the virtual bone model.

Therefore, the target acquisition unit 341 performs coordinate transformation by multiplying the positional coordinates of a target point defined in the implant coordinate system by a transformation matrix between the bone model coordinate system and the implant coordinate system. Such a coordinate transformation method of transforming the coordinates of a point in one coordinate system into the coordinates in another coordinate system is well-known, and therefore detailed descriptions thereof will be omitted for the convenience of description.

The target acquisition unit 341 may set the number of acquired cutting target points differently according to the shapes or patterns of the cutting path when acquiring the positions of the plurality of cutting target points.

Figure 4A:
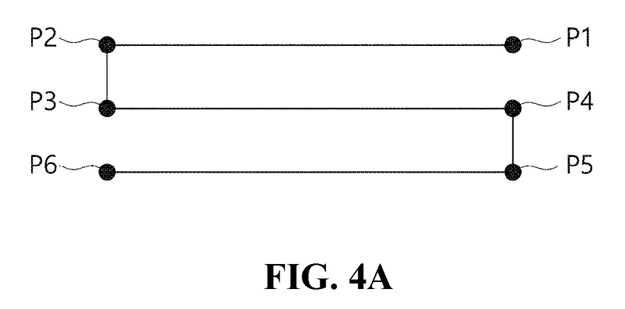
FIGS. 4A-4B are reference diagrams for explaining an example where the positions of cutting target points are acquired by a target acquisition unit according to an embodiment of the disclosure.
Figure 4B:
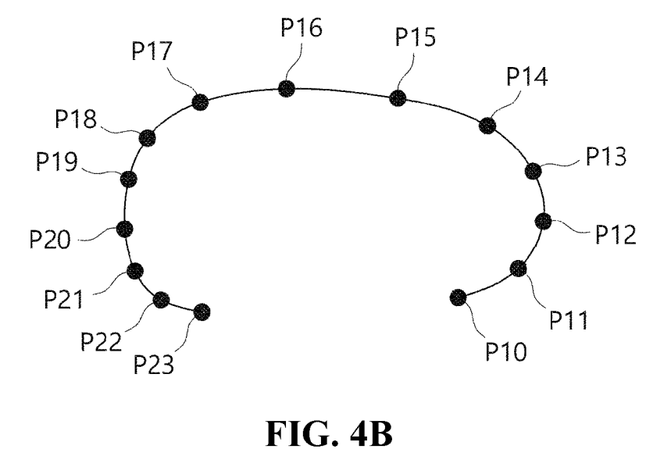

FIGS. 4A-4B are reference diagrams for explaining an example where the positions of the cutting target points are acquired by the target acquisition unit 341 according to an embodiment of the disclosure.

Referring to FIG. 4A shows an example where the cutting path is formed by a combination of straight lines, and FIG. 4B shows an example where the cutting path is formed by a curved line.

When the cutting path is formed by a straight line or a combination of straight lines as shown in FIG. 4A, the target acquisition unit 341 may be configured to acquire the positions of the cutting target points corresponding to two points, i.e., a starting point of one straight-line path and an ending point of the corresponding straight-line path. For example, when the cutting path is formed by a combination of five straight lines as shown in FIG. 4A, the target acquisition unit 341 may acquire the positions p1 to p6 corresponding to the starting and ending points of each straight line whenever the path is switched from one straight line to another straight line. In this case, the straight lines forming the cutting path are connected to each other, and therefore the points p2, p3, p4 and p5 serve as not only the ending points of one straight line but also the starting points of another connected straight line.

For reference, FIG. 4A shows an example that the plurality of straight lines are connected to each other. However, the cutting path may be given in the form of a plurality of separated straight lines, a combination of a plurality of separated straight lines, etc.

Meanwhile, when the cutting path is formed by a curved line as shown in FIG. 4B, the target acquisition unit 341 may be configured to acquire not only the starting and ending points of the curved line but also the positions of more cutting target points than those of the straight-line path, according to the curvature of the curved line, the rate of change in the curvature, and direction change. For example, the target acquisition unit 341 may acquire the positions of more points as the curvature or the rate of change in the curvature increases. For reference, FIG. 4B shows an example that fourteen positions corresponding to p10 to p23 are acquired.

The robot position calculation unit 343 is configured to calculate the current cutting position of the surgical robot 100, which corresponds to the surgical progress of the surgical robot 100, among the cutting target points acquired by the target acquisition unit 341. Here, the current cutting position of the surgical robot 100 may include an estimated position, or an actual position at which the surgical robot 100 is actually performing the cutting with the surgical tool.

In other words, the robot position calculation unit 343 may calculate the current cutting position of the surgical robot 100 based on the cutting speed of the surgical robot 100 which is stored in the memory unit 330, the time it takes for the surgical robot 100 to perform the cutting, and a distance between the cutting target points acquired by the target acquisition unit 341. For example, when it is assumed that a cutting tool of the surgical robot 100 is turned on to start the cutting operation at time t1, the current time is t2, and the surgical robot 100 has a cutting speed of v based on the surgery plan information, a distance traveled by the surgical robot 100 is (t2−t1)*v. In this way, it is possible to estimate where the current cutting position of the surgical robot 100 is among the plurality of cutting target points. In this case, when the cutting speed of the surgical robot 100 is planned to be varied depending on the cutting positions based on the surgery plan information, the current cutting position is estimated based on the cutting speed planed corresponding to the cutting position.

Further, the robot position calculation unit 343 may calculate the current cutting position by grasping the actual position on the surgical robot 100 on the virtual bone model based on information about the position of the surgical robot 100 received from the tracking device 200, robot calibration performed before surgery, and registration between the image of the virtual bone model and the space of the robot.

The robot position calculation unit 343 may calculate only one of the foregoing estimated cutting position and the actual cutting position, but may calculate both of them.

Because the cutting position of the surgical robot 100 is changed every moment in the surgical process, the robot position calculation unit 343 calculates and updates the changing current cutting position in real time.

The GUI providing unit 345 is configured to generate graphics representing the surgery progress information on the virtual bone model of the surgical target bone. In other words, the GUI providing unit 345 generates graphics based on the surgery progress information including the positions of the cutting target points acquired through the target acquisition unit 341 and the current cutting position of the surgical robot 100 calculated by the robot position calculation unit 343. The surgery progress information generated graphically is displayed being overlapped on the virtual bone model by the display unit 320. The GUI providing unit 345 may include a graphic card to transmit the generated data to the display unit 320.

The GUI providing unit 345 generates graphics based on figures respectively corresponding to the plurality of cutting target points acquired by the target acquisition unit 341, a cutting line (e.g., a straight line or a curved line) formed by connecting the cutting target points according to a cutting sequence of the surgical robot 100, and a figure corresponding to the current cutting position of the surgical robot 100 calculated by the robot position calculation unit 343. The cutting line that the surgical robot 100 has already passed and the cutting line that the surgical robot 100 is currently passing may be generated to be graphically distinguished from each other with respect to the current cutting position. For example, the passed cutting line and the currently passing cutting line may be different in color, transparency, line flickering, line type, etc.

Further, when the robot position calculation unit 343 calculates both the estimated cutting position and the actual cutting position, the two positions may be displayed with different shapes, colors, etc. to be distinguished from each other, so that a user can easily monitor the surgical progress by checking the difference in distance between the two positions with the naked eye.

Meanwhile, the GUI providing unit 345 may set whether to display the surgery progress information through the display unit 320 according to the on and off states of the surgical robot 100, and may set a displaying type. For example, when the surgical tool for the cutting of the surgical robot 100 is turned on, the surgery progress information may be displayed to be overlapped on the virtual bone model. On the other hand, when the surgical tool is turned off, the surgery progress information may not be displayed. Alternately, even when the surgical tool is turned off, the surgery progress information may be displayed with color, of which visibility is relatively low, like gray, or may be displayed to look pale with high transparency.

The display unit 320 may display state information such as on/off information of the surgical tool (or the cutting tool), the load applied to the surgical tool, the speed of the surgical robot 100, etc. as well as the surgery progress information through the GUI providing unit 345. In this case, the speed of the surgical robot 100 may include the speed based on the surgical planning, or the actual speed based on a value sensed during the cutting process.

The view switching unit 347 is configured to switch a view of a virtual bone model displayed on the display unit 320 according to parts of a surgical target bone that undergoes the cutting of the surgical robot 100.

Figure 5A:
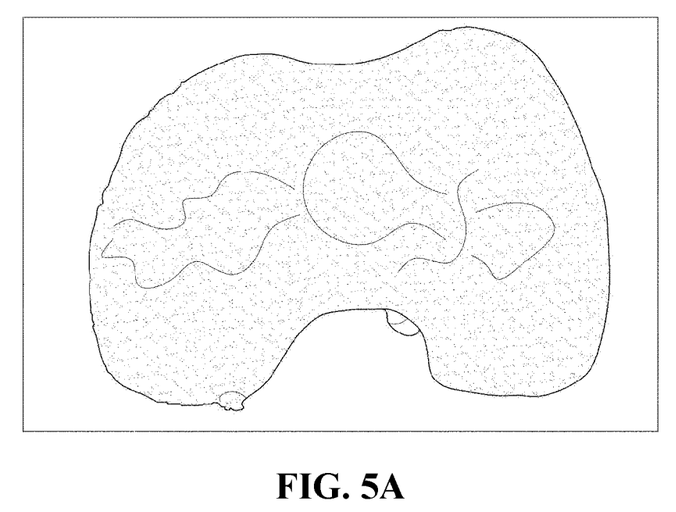
FIGS. 5A-5B show examples of a screen for explaining an operation of a view switching unit according to an embodiment of the disclosure.
Figure 5B:
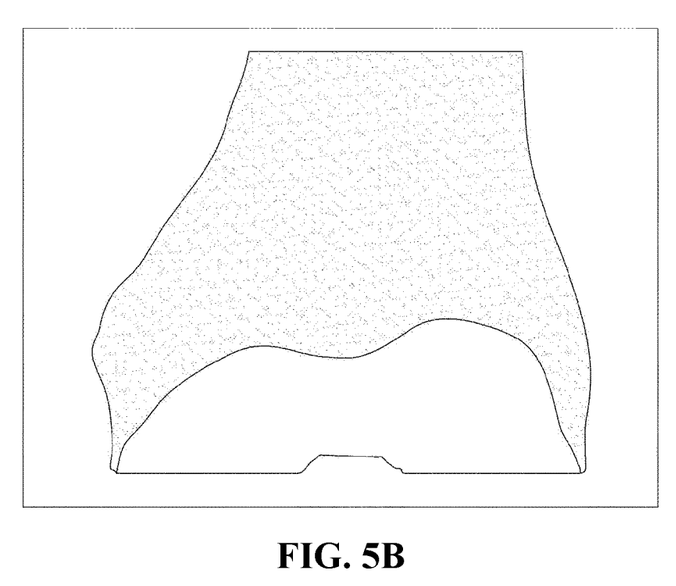

FIGS. 5A-5B show examples of a screen for explaining an operation of the view switching unit 347 according to an embodiment of the disclosure. When the surgical robot 100 cuts the distal of the femur as shown in FIG. 5A, the view is set to make the center of the distal be located in the front of the screen and visible clearly. When the anterior of the femur is cut as shown in FIG. 5B, the view is switched to make the center of the anterior be located in the front of the screen.

The view switching unit 347 is configured to perform view switching based on a user input, which is related to which part of the surgical target bone is currently being cut, through a keyboard, a mouse, or the like a user input unit (not shown) for receiving the user input. Alternatively, the view switching unit 347 is configured to automatically perform view switching by receiving information about the position of the surgical robot 100 tracked by the tracking device 200 or information detected by the surgical robot 100, and grasping which direction or position a robot arm of the surgical robot 100 moves with respect to the surgical target bone or a direction changed state of the surgical tool.

The view switching unit 347 may rotate the virtual bone model or switch the view based on the Euler angle, a rotation matrix, quaternion improved in the gimbal lock problem, etc. In this way, an object displayed on a screen is rotated or changed in the direction of view by various well-known operations, and thus detailed descriptions thereof will be omitted for the convenience of description.

Further, the view switching unit 347 may be configured to not only switch the view but also enlarge or reduce the virtual bone model by a predetermined magnification in consideration of the size of a cut surface, and the number of cutting target points displayed on the cut surface of the virtual bone model. For example, when the cut surface is relatively small, the virtual bone model may be enlarged to be seen largely. Even when the number of cutting target points to be displayed being overlapped on the virtual bone model is large, the virtual bone model may be enlarged so that a user can easily distinguish the cutting target points.

The notification unit 349 is configured to provide a notification to a user when the cutting is performed by the surgical robot 100 outside the cutting path based on the surgery plan information. The notification unit 349 may be implemented including a loudspeaker to provide a notification with a sound such as a warning sound, or may provide a visual notification displaying a message on the display unit 320.

The notification unit 349 may provide a notification when the actual cutting position of the surgical robot 100 based on the position information of the surgical robot 100 received from the tracking device 200 is far by more than a predetermined distance away from the current cutting position of the surgical robot 100 estimated by the robot position calculation unit 343. Further, the notification unit 349 may provide a notification when the actual cutting position calculated based on the information received from the tracking device 200 deviates from the cutting path based on the surgery plan information by more than a predetermined criterion.

With the foregoing configuration, the surgery information providing device 300 according to the disclosure displays the surgery progress information such as the cutting path information based on the surgical planning, the current cutting position of the surgical robot 100, the state of the robot, etc. on the virtual bone model, thereby helping a user to recognize the surgical progress and monitor the surgical progress.

Figure 6:
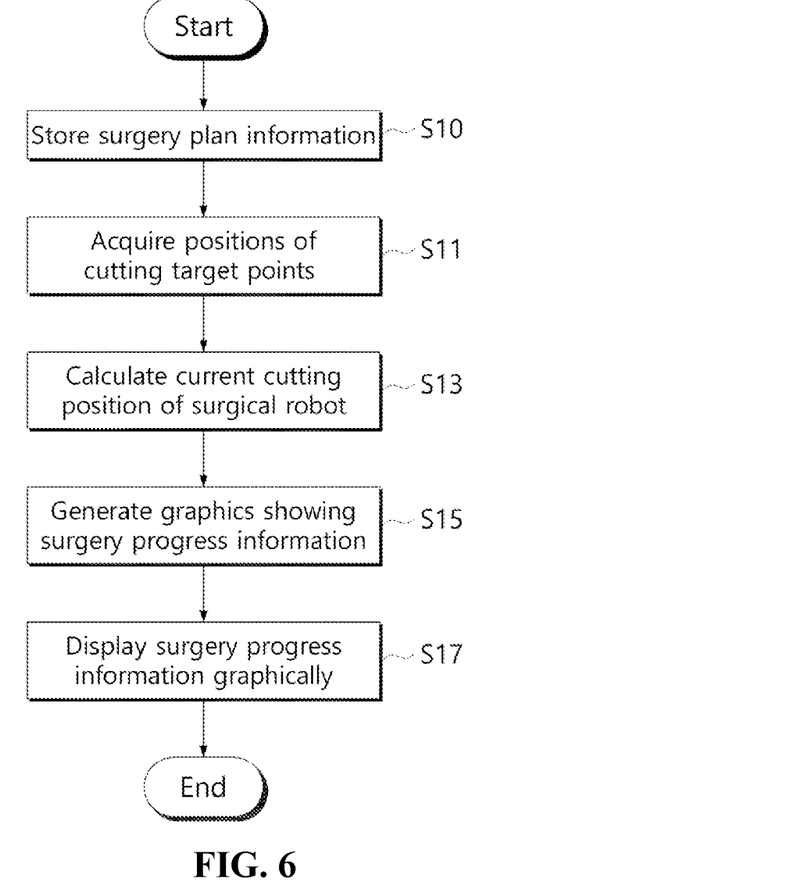
FIG. 6 is a flowchart showing a method of providing information about joint replacement robotic surgery according to an embodiment of the disclosure.

FIG. 6 is a flowchart showing a method of providing information about joint replacement robotic surgery according to an embodiment of the disclosure. Below, organic operations of the surgery information providing device 300 configured as above will be described with reference to FIG. 6. As necessary, repetitive descriptions to those of the foregoing embodiments will be avoided.

Referring to FIG. 6, the method of providing information about the joint replacement robotic surgery according to an embodiment of the disclosure is premised on storing the information about the surgery plan made by preoperative planning in the memory unit 330 (S10). The preoperative planning may be based on a patient's medical images taken before surgery through various types of well-known planning software. Through the preoperative planning, information about the surgery plans for the types, shapes, and sizes of implants to be implanted into the surgical target bones; the implanting position/direction/angle of the implant; the cutting path along with the surgical target bone is cut to implant the corresponding implant; the cutting speed based on the density of bone to be cut; etc. is generated.

When the joint replacement robotic surgery system 1 with the foregoing configuration is prepared in a surgical site, robot calibration for establishing a relationship between a vision sensor reference coordinate system of the tracking device 200 and a reference coordinate system of the robot, based on the well-known art; registration between the surgical target bone and the medical image so as to apply the surgery plan made based on the medial image to the actual surgical target bone; robot registration for establishing a relationship between the position/pose of the robot and the position/pose of the robot marker; etc. are performed, and the robotic surgery is started according to the surgery plan.

When the robotic surgery is started, the target acquisition unit 341 acquires the positions of the plurality of cutting target points forming the cutting path based on the stored surgery plan information (S11). In this case, the cutting path based on the surgery plan information is defined in the implant coordinate system. To display the cutting path on the virtual bone model, the coordinate transformation is required to transform the positional coordinate values in the implant coordinate system into the positional coordinate values in the virtual bone model coordinate system. Meanwhile, when the target acquisition unit 341 acquires the positions of the plurality of cutting target points, the number of cutting target points may be set differently according to the shapes or patterns of the cutting path.

Then, the robot position calculation unit 343 calculates the current cutting position of the surgical robot 100 among the cutting target points based on the surgery progress of the surgical robot (S13). Here, the current cutting position may be an estimated position estimated based on the time it takes for the surgical robot 10 to perform the cutting, and the cutting speed according to the surgery plan, or the actual position on the virtual bone model calculated based on the position information of the surgical robot tracked by the tracking device 200.

Next, the GUI providing unit 345 generates graphics showing the surgery progress information based on the data acquired above (S15). In this case, figures respectively corresponding to the plurality of cutting target points acquired by the target acquisition unit 341, a cutting line (e.g., a straight line or a curved line) formed by connecting the cutting target points according to a cutting sequence of the surgical robot 100, and a figure corresponding to the current cutting position of the surgical robot 100 calculated by the robot position calculation unit 343 may be generated as graphics on the virtual bone model corresponding to the surgical target bone.

The display unit 320 displays the surgery progress information generated as graphics by the GUI providing unit 345 and state information detected by the surgical robot 100 on the virtual bone model (S17).

FIGS. 7 to 10 show examples of images displayed on the display unit 320 according to an embodiment of the disclosure.

Figure 7:
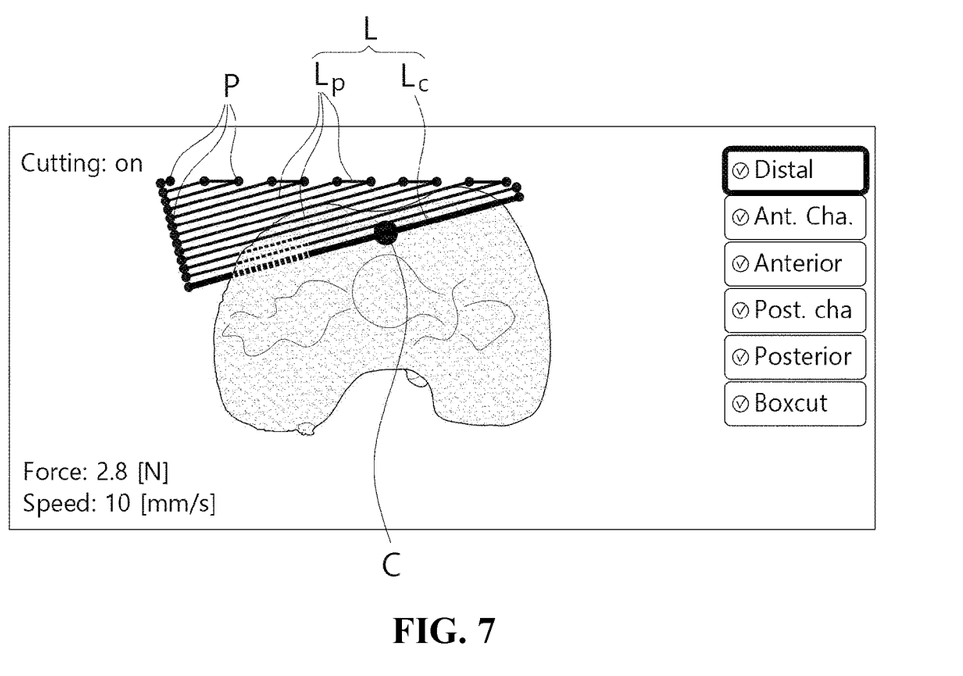
FIGS. 7 and 8 show examples of images displayed when a surgical robot cuts a distal portion of a femur.
Figure 8:
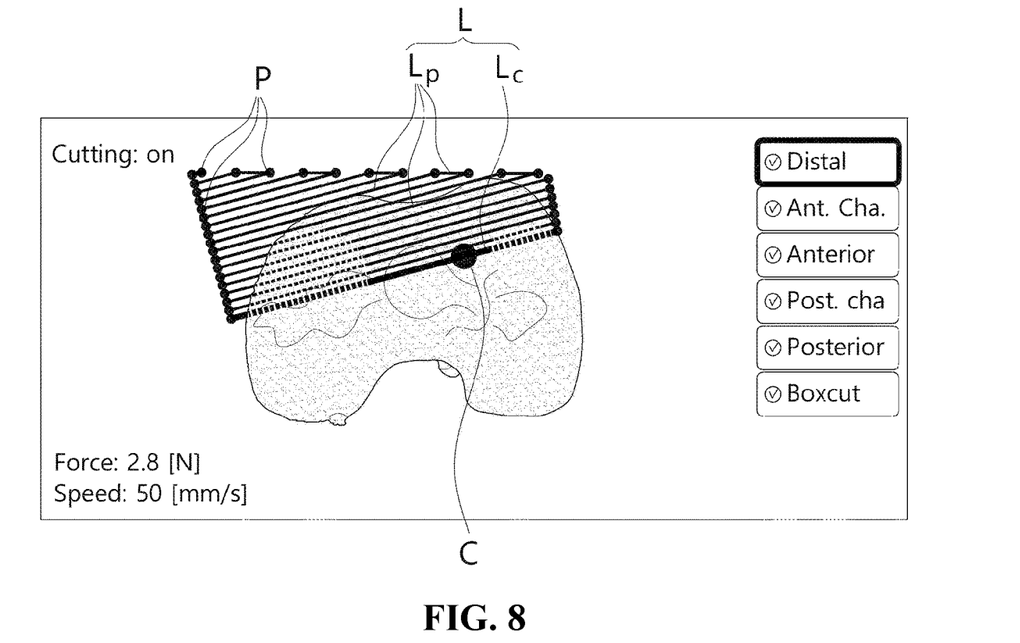

FIGS. 7 and 8 show images displayed when the surgical robot 100 cuts a distal portion of a femur in the state that the surgical tool of the surgical robot 100 is turned on. For reference, FIG. 8 shows a state in which the cutting is further performed as compared with that of FIG. 7.

The current cutting position C of surgical robot 100 is displayed in a spherical shape, and the plurality of cutting target points P are displayed in a spherical shape smaller than that of the current cutting position C. However, this is merely an example of the display. Besides the spherical shape, the current cutting position C and the cutting target points P may be displayed in various shapes, sizes and colors. For example, the spherical shape of the current cutting position C may be displayed in red, and the spherical shape of the cutting target points P may be displayed in yellow, so that the current cutting position C and the cutting target points P can be displayed to be distinguished from each other.

Further, referring to FIGS. 7 and 8, a cutting line LP that the surgical robot 100 has already passed and a cutting line LC that the surgical robot 100 is currently passing may be different in color, saturation, brightness, line thickness, etc. to be distinguished from each other in such a manner that the cutting line LP is colored in yellow, and the cutting line LC is colored in red, thereby helping a user to intuitively grasp a part in which the cutting is currently being performed.

Meanwhile, all the plurality of cutting target points P and cutting lines L for the whole cutting path based on the surgery plan may be displayed from the beginning. However, as shown in FIGS. 7 and 8, the cutting target points P and the cutting lines L may be displayed in sequence according to the cutting progress of the surgical robot 100.

As the cutting is performed, the cutting position of the surgical robot 100 is continuously changed, and therefore the current cutting position C is displayed moving like a moving picture on the display unit 320 along the cutting line L in real time, reflecting such change of the cutting position.

Meanwhile, "Cutting: On" is displayed at an upper left corner of the screen, thereby showing that the surgical tool of the surgical robot 100 is turned on. Further, at a lower left corner of the screen, the load applied to the surgical tool is displayed in units of N, and the cutting speed is displayed in units of mm/s. In this case, the cutting speed may be a planned speed based on the surgical planning information, or an actual cutting speed.

Figure 9:
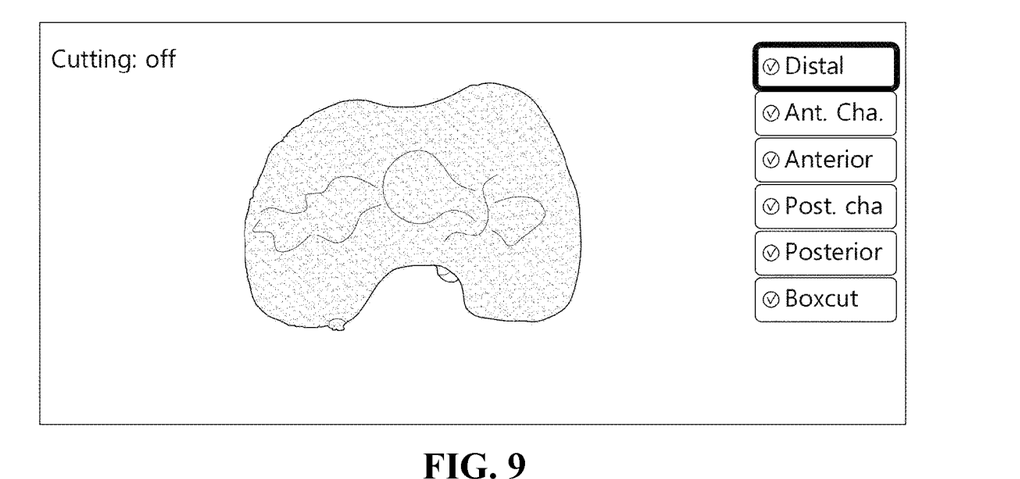
FIG. 9 shows an example of an image displayed when a surgical tool of a surgical robot is turned off.

FIG. 9 shows an example of an image displayed when the surgical tool of the surgical robot 100 is turned off. Referring to FIG. 9, only the state information, i.e., "Cutting: Off" is displayed at the upper left corner, and other state information or surgery progress information is not displayed. This is merely an example. As described above, such displayed information may be varied in color, transparency, etc. so that "On" and "Off" can be distinguished from each other.

Figure 10:
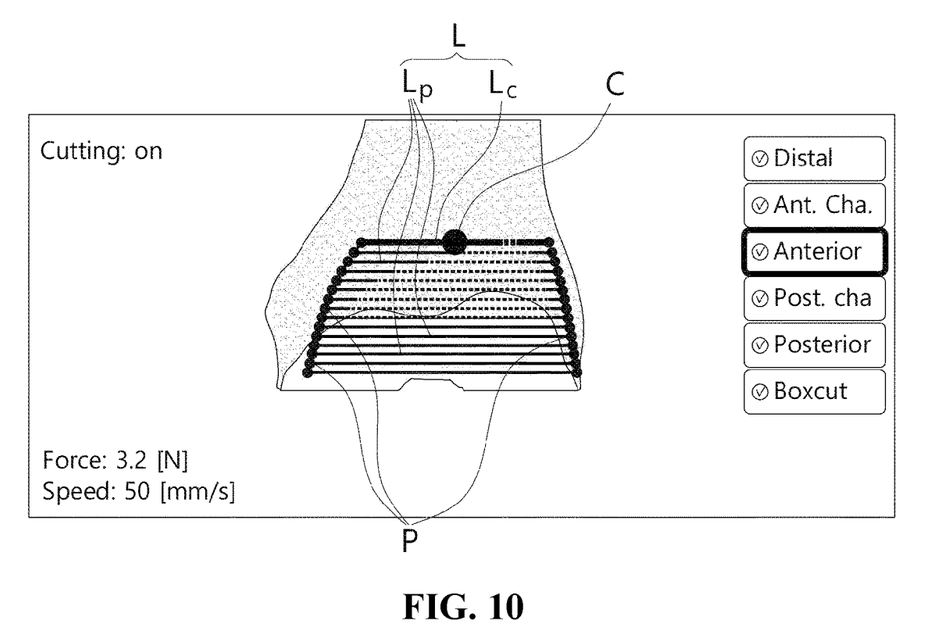
FIG. 10 shows an example of an image displayed when a surgical robot cuts an anterior portion of a femur.

FIG. 10 shows an example of an image displayed when the surgical robot 10 cuts an anterior portion of a femur. Referring to FIG. 10, the current cutting position C, the cutting line L, the plurality of cutting target points P, and the state information of the surgical robot are displayed like those of FIGS. 7 and 8. However, as compared with FIGS. 7 and 8 showing the state of cutting the distal portion, FIG. 10 is changed in the point of view so that the anterior portion can be clearly seen on the screen.

Thus, the view switching unit 347 may delete a previously displayed surgery progress information and switch the view over to another point of view when the surgical robot 100 ends cutting a specific portion and starts cutting another portion.

Meanwhile, appropriate addition or change can be made in the operations of the method described with reference to FIG. 6 as necessary. For example, when the actual cutting position of the surgical robot 100 is far by more than a predetermined distance away from the estimated current cutting position of the surgical robot 100 or when the actual cutting position of the surgical robot 100 deviates from the cutting path based on the surgery plan information by more than a predetermined criterion, an operation of providing a notification by the notification unit 349 may be added.

As described above, by the device 300 and method for providing information about the joint replacement robotic surgery according to the disclosure, the cutting path planned before surgery, the surgery progress information about which position the surgical robot 100 is currently passing on the cutting path, and the state information of the surgical robot 100 are provided to a user, thereby helping a user to recognize the surgical progress and monitor the surgical progress.

The embodiments described herein may be implemented using hardware components and software components. For example, the hardware components may include microphones, amplifiers, band-pass filters, audio to digital convertors, non-transitory computer memory and processing devices. A processing device may be implemented using one or more general-purpose or special purpose computers, such as, for example, a processor, a controller and an arithmetic logic unit (ALU), a digital signal processor, a microcomputer, a field programmable array (FPGA), a programmable logic unit (PLU), a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

Although a few embodiments have been described above with reference to the limited drawings, various modifications and changes can be made from the foregoing description by a person having ordinary knowledge in the art. For example, suitable results may be achieved if the described techniques are performed in a different order, and/or if components in a described system, architecture, device, or circuit are combined in a different manner and/or replaced or supplemented by other components or their equivalents. Therefore, other implementations, other embodiments, and equivalents to claims also fall within the scope of the appended claims.

The invention claimed is:

1. A device for providing information about joint replacement robotic surgery, the device comprising:
    a memory unit configured to store surgery plan information set before surgery including a cutting path of a surgical target bone;
    a target acquisition unit configured to acquire positions of a plurality of cutting target points forming the cutting path based on the surgery plan information, wherein the target acquisition unit acquires starting points and ending points of each straight line as the cutting target points when the cutting path is formed of one more straight lines;
    a robot position calculation unit configured to calculate a current cutting position of a surgical robot among the cutting target points based on surgery progress of the surgical robot, wherein the robot position calculation unit calculates an estimated cutting position which is estimated based on a cutting speed of the surgical robot according to the surgery plan information and a distance between the cutting target points, and an actual cutting position based on information received from a tracking device configured to track the position of the surgical robot, respectively;
    a graphic user interface (GUI) providing unit configured to generate graphics that represent surgery progress information comprising a current cutting position of the surgical robot and positions of the cutting target points on a virtual bone model corresponding to the surgical target bone, wherein the GUI providing unit generates figures respectively corresponding to the plurality of cutting target points, a cutting line formed by connecting the cutting target points, and figures respectively corresponding to the estimated cutting position of the surgical robot and the actual cutting position of the surgical robot;
    a display unit configured to display the virtual bone model and the surgery progress information; and
    a view switching unit configured to automatically switch a view of the virtual bone model according to parts of the surgical target bone that undergoes cutting by the surgical robot, a position of robot arm of the surgical robot with respect to the surgical target bone, and a direction changed state of surgical tool.

2. The device of claim 1, wherein the view switching unit enlarges or reduces the virtual bone model by a predetermined magnification based on a size of cut surface of the virtual bone model, and a number of the cutting target points displayed on the cut surface.

3. The device of claim 1, wherein the target acquisition unit performs coordinate transformation from a position of the cutting target point in a first coordinate system based on an implant to be replaced in the surgical target bone to a position in a second coordinate system based on the virtual bone model.

4. The device of claim 1, further comprising a notification unit configured to provide a notification when the actual cutting position is far by more than a predetermined distance away from the estimated cutting position.

5. The device of claim 1, further comprising a signal receiver configured to receive state information of the surgical robot from the surgical robot,
wherein the display unit displays the state information of the surgical robot.

6. The device of claim 1, wherein the GUI providing unit sets whether to display the surgery progress information through the display unit based on on/off states of the surgical robot.

7. The device of claim 1, wherein the GUI providing unit generates graphics so that the cutting line that the surgical robot has already passed and the cutting line that the surgical robot is currently passing can be distinguished from each other with respect to the current cutting position of the surgical robot calculated by the robot position calculation unit.

8. A method of providing information about joint replacement robotic surgery, which are performed by a joint replacement robotic surgery information providing device that provides information about joint replacement robotic surgery, the method comprising the steps of:
storing surgery plan information set before surgery including a cutting path of a surgical target bone;
acquiring positions of a plurality of cutting target points forming the cutting path based on the surgery plan information, wherein the cutting target points are starting points and ending points of each straight line when the cutting path is formed of one more straight lines;
calculating a current cutting position of a surgical robot among the cutting target points based on surgery progress of the surgical robot, wherein an estimated cutting position which is estimated based on a cutting speed of the surgical robot according to the surgery plan information and a distance between the cutting target points, and an actual cutting position based on information received from a tracking device configured to track the position of the surgical robot are calculated as the current cutting position, respectively;
generating graphics that represent surgery progress information comprising a current cutting position of the surgical robot and positions of the cutting target points on a virtual bone model corresponding to the surgical target bone, wherein figures respectively corresponding to the plurality of cutting target points, a cutting line formed by connecting the cutting target points, and figures respectively corresponding to the estimated cutting position of the surgical robot and the actual cutting positions of the surgical robot are generated;
displaying the virtual bone model and the surgery progress information on a display unit; and
automatically switching a view of the virtual bone model according to parts of the surgical target bone that undergoes cutting by the surgical robot, a position of robot arm of the surgical robot with respect to the surgical target bone, and a direction changed state of surgical tool.

* * * * *